(12) United States Patent
Demeyere et al.

(10) Patent No.: US 8,506,940 B2
(45) Date of Patent: Aug. 13, 2013

(54) AQUEOUS COMPOSITIONS COMPRISING VESICLES HAVING CERTAIN VESICLE PERMEABILITY

(75) Inventors: Hugo Jean-Marie Demeyere, Merchtem (BE); Gunnel Ingegard Matilda Johnasson, Göteborg (SE); Mangus Bo Nydén, Billdal (SE)

(73) Assignee: The Procter & Gamble Company, Cincinnati, OH (US)

(*) Notice: Subject to any disclaimer, the term of this patent is extended or adjusted under 35 U.S.C. 154(b) by 373 days.

(21) Appl. No.: 12/793,912

(22) Filed: Jun. 4, 2010

(65) Prior Publication Data

US 2010/0239513 A1  Sep. 23, 2010

Related U.S. Application Data

(63) Continuation of application No. 10/967,758, filed on Oct. 18, 2004, now abandoned.

(60) Provisional application No. 60/511,732, filed on Oct. 16, 2003.

(51) Int. Cl.

| | | |
|---|---|---|
| *A61Q 13/00* | (2006.01) | |
| *A61Q 5/12* | (2006.01) | |
| *C07C 211/00* | (2006.01) | |
| *A61K 8/41* | (2006.01) | |
| *C07C 211/62* | (2006.01) | |
| *C11D 1/62* | (2006.01) | |
| *C11D 3/30* | (2006.01) | |

(52) U.S. Cl.
CPC .............. *A61Q 13/00* (2013.01); *A61K 8/416* (2013.01); *A61Q 5/12* (2013.01); *C07C 211/62* (2013.01); *C11D 1/62* (2013.01); *C11D 3/30* (2013.01)
USPC .......... 424/70.1; 424/450; 510/527; 514/642; 514/705; 512/2

(58) Field of Classification Search
None
See application file for complete search history.

(56) References Cited

U.S. PATENT DOCUMENTS

| | | | |
|---|---|---|---|
| 4,111,854 A | 9/1978 | Spadini et al. | |
| 4,424,134 A | 1/1984 | Sissin et al. | |
| 4,550,862 A | 11/1985 | Barker et al. | |
| 4,767,547 A | 8/1988 | Straathof et al. | |
| 4,981,239 A | 1/1991 | Cappel et al. | |
| 5,089,148 A | 2/1992 | Van Blarcom et al. | |
| 5,382,376 A | 1/1995 | Michael et al. | |
| 5,409,621 A | 4/1995 | Ellis et al. | |
| 5,531,910 A | 7/1996 | Severns et al. | |
| 5,545,340 A | 8/1996 | Wahl et al. | |
| 5,545,350 A | 8/1996 | Baker et al. | |
| 5,562,849 A | 10/1996 | Wahl et al. | |
| 5,574,179 A | 11/1996 | Wahl et al. | |
| 5,668,102 A | 9/1997 | Severns et al. | |
| 5,874,396 A | 2/1999 | Littig et al. | |
| 5,876,705 A | 3/1999 | Uchiyama et al. | |
| 6,093,691 A * | 7/2000 | Sivik et al. .................... | 510/515 |

(Continued)

FOREIGN PATENT DOCUMENTS

| | | |
|---|---|---|
| WO | WO 96/41842 | 12/1996 |
| WO | WO 97/00919 | 1/1997 |

(Continued)

*Primary Examiner* — Frederick Krass
*Assistant Examiner* — Isaac Shomer
(74) *Attorney, Agent, or Firm* — James F. McBride; Melissa G. Krasovec

(57) ABSTRACT

Compositions for effectively delivering a water-soluble active material to a surface comprise:

(a) from about 1% to about 30%, by weight of the composition, of a dialkyl quaternary ammonium compound having the formula:

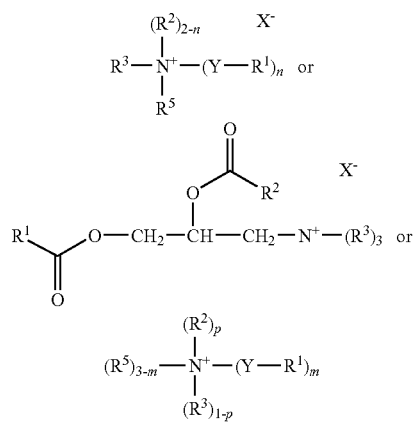

wherein $R^1$ and $R^2$ are independently $C_{12}$ to $C_{20}$ saturated alkyl chains; Y is

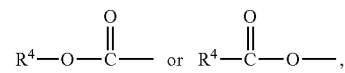

wherein $R^4$ is ethyl or isopropyl; $R^3$ and $R^5$ are independently methyl, ethyl, hydroxyethyl, or hydroxypropyl; m is 1, 2, or 3; n is 1 or 2; p is 0 or 1; and $X^-$ is a suitable anion;

(b) from about 0.01% to about 10%, by weight of the composition, of water-soluble active material having a ClogP of less than about 2.0; and (c) at least about 60%, by weight of the composition, of water;

wherein the compositions contain vesicles having a vesicle permeability index of less than about 1.3. Processes to make the compositions comprise the steps of dispersing the dialkyl quaternary ammonium compound and the water-soluble active material in an aqueous solution to form vesicles having a vesicle permeability index of less than about 1.3.

11 Claims, No Drawings

(56) References Cited

U.S. PATENT DOCUMENTS

| | | |
|---|---|---|
| 6,200,586 B1 | 3/2001 | Lambie et al. |
| 6,218,354 B1 | 4/2001 | Demeyere et al. |
| 6,242,526 B1 | 6/2001 | Siddiqui et al. |
| 6,323,172 B1 | 11/2001 | Trinh et al. |
| 6,468,515 B1 | 10/2002 | Uchiyama et al. |
| 6,479,566 B2 | 11/2002 | Lines et al. |
| 6,589,517 B1 | 7/2003 | McKelvey et al. |
| 2003/0013799 A1 | 1/2003 | Crooks et al. |
| 2003/0114338 A1 | 6/2003 | Grainger et al. |

FOREIGN PATENT DOCUMENTS

| | | |
|---|---|---|
| WO | WO 97/01326 | 1/1997 |
| WO | WO 98/18444 | 5/1998 |
| WO | WO 98/22085 | 5/1998 |

* cited by examiner

AQUEOUS COMPOSITIONS COMPRISING VESICLES HAVING CERTAIN VESICLE PERMEABILITY

CROSS REFERENCE TO RELATED APPLICATION

This application is a continuation of U.S. patent application Ser. No. 10/967,758, filed Oct. 18, 2004 now abandoned, which claims priority to U.S. Provisional Application Ser. No. 60/511,732, filed Oct. 16, 2003, the disclosure of which is incorporated by reference herein.

FIELD OF THE INVENTION

The present invention relates to aqueous compositions comprising vesicles having a vesicle permeability index of less than about 1.3 to facilitate the delivery of water-soluble active materials having a ClogP of less than about 2.0 to surfaces being treated with the compositions.

BACKGROUND OF THE INVENTION

A number of commercialized products, such as fabric softeners, hard surface cleaners, hair conditioners, agrochemical products and paints, contain active materials that are water-soluble. Oftentimes, these products contain water-soluble active materials that are intended to be deposited onto a surface being treated with the product. However, if these water-soluble materials are in a highly aqueous environment, it can be difficult to effectively deposit the water-soluble active materials onto the surface. For example, a fabric softening composition is typically added to the rinse solution in a fabric laundering process, which contains a large volume of water. Once the rinse cycle is complete, the rinse solution is discarded down the drain, usually taking a large portion of the water-soluble active materials with it. Thus only a small portion of the water-soluble active materials is actually deposited on the treated fabrics.

It has thus been desired to develop a composition containing water-soluble active materials such that the composition can effectively deposit the water-soluble active materials to a surface being treated with the composition.

SUMMARY OF THE INVENTION

The present invention relates to compositions comprising:

(a) from about 1% to about 30%, by weight of the composition, of a dialkyl quaternary ammonium compound having the formula:

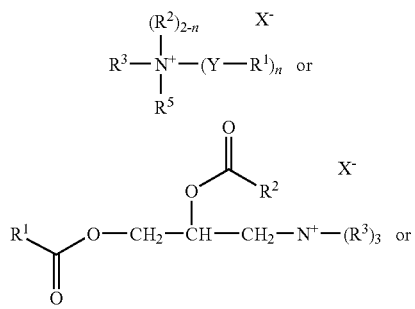

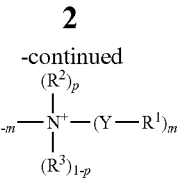

-continued

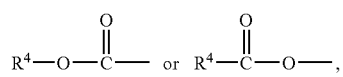

wherein $R^1$ and $R^2$ are independently $C_{12}$ to $C_{20}$ saturated alkyl chains; Y is $$R^4-O-\overset{O}{\underset{\|}{C}}-\quad \text{or} \quad R^4-\overset{O}{\underset{\|}{C}}-O-,$$

wherein $R^4$ is ethyl or isopropyl; $R^3$ and $R^5$ are independently methyl, ethyl, hydroxyethyl, or hydroxypropyl; m is 1, 2, or 3; n is 1 or 2; p is 0 or 1; and $X^-$ is a suitable anion;

(b) from about 0.01% to about 10%, by weight of the composition, of water-soluble active material having a ClogP of less than about 2.0; and (c) at least about 60%, by weight of the composition, of water;

wherein the compositions contain vesicles having a vesicle permeability of less than about 1.3, preferably less than about 1.1, and more preferably less than about 1.0. The fully saturated dialkyl quaternary ammonium compounds of the present compositions, containing at least one ester bond, have been found to form vesicles that can encapsulate water-soluble active materials and that exhibit a low rate of diffusion across the membrane of the vesicles. As the vesicles deposit onto the surfaces being treated with the compositions, the vesicles are able to effectively deliver water-soluble active materials to the surface, which previously has been difficult to achieve.

The present invention further relates to a process for making the present compositions comprising the steps of dispersing the dialkyl quaternary ammonium compound and the water-soluble active material in an aqueous solution to form vesicles having a vesicle permeability index of less than about 1.3.

DETAILED DESCRIPTION OF THE INVENTION

Vesicular Compositions

The present invention relates to compositions containing vesicles to facilitate the delivery of water-soluble active materials to surfaces treated with the present compositions. As used herein the term "vesicle" means one or more bilayers arranged in a closed, usually spherical geometry, said bilayer comprises quaternary ammonium agent as described hereinabove. In the compositions herein, the vesicles are preferably substantially spherical. The presence of vesicles in the present compositions can be detected by microscopic analysis (e.g., polarised light microscopy at a magnification of 60×). Preferably, the vesicles in the present compositions have a number average size of from about 50 nm to about 20 μm, more preferably from about 100 nm to about 5 μm, most preferably from about 200 nm to about 2 μm as determined by photon correlation spectroscopy.

The vesicles in the present compositions are generally formed by dispersing the molten dialkyl quaternary ammonium compound in hot water having a temperature above the transition temperature of the dialkyl quaternary ammonium compound. It is believed that the vesicles envelope the water-soluble active materials and then can effectively deliver these species to a surface being treated.

The vesicles in the present compositions exhibit a particular vesicle permeability as measured according to the test method described herein. The vesicle permeability of the vesicles formed can be affected by the temperature and by the structure of the dialkyl quaternary ammonium compounds, more specifically by the degree of unsaturation and the presence or the absence of linking groups between the alkyl chain and the nitrogen, such as esters.

The compositions of the present invention will typically have a pH of from about 2 to about 7, preferably from about 2 to about 6, and more preferably from about 2.5 to about 5.0.

Dialkyl Quaternary Ammonium Compound

The present compositions comprise a dialkyl quaternary ammonium compound having the formula:

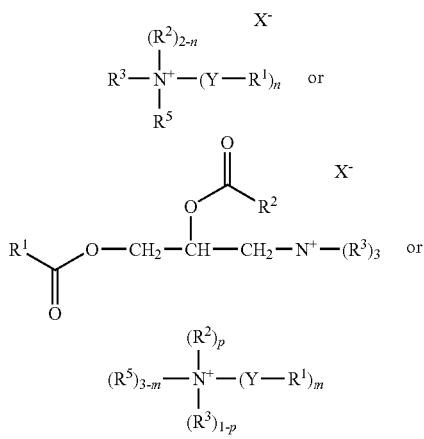

wherein $R^1$ and $R^2$ are independently $C_{12}$ to $C_{20}$ saturated alkyl chains; Y is

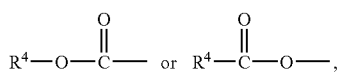

wherein $R^4$ is ethyl or isopropyl; $R^3$ and $R^5$ are independently methyl, ethyl, hydroxyethyl, or hydroxypropyl; m is 1, 2, or 3; n is 1 or 2; and p is 0 or 1. The counterion, $X^-$ in the above compounds, can be any compatible anion, preferably the anion of a strong acid, for example, chloride, bromide, methylsulfate, ethylsulfate, sulfate, nitrate and the like, more preferably chloride or methyl sulfate.

Suitable dialkyl quaternary ammonium compounds of the present invention include alkylchains wherein $R^1$ and $R^2$ are $C_{16}$ or $C_{18}$ or hardened tallow or hardened palm or mixtures thereof. Non-limiting examples of dialkyl quaternary ammonium compounds include N,N-di(stearoyl-oxy-ethyl)-N,N-dimethyl ammonium chloride; N-stearyl-N-(stearoyl-oxy-ethyl)-N,N-dimethyl ammonium chloride; N,N-di(stearoyl-oxy-ethyl)-N-methyl, N-(2-hydroxyethyl) ammonium methylsulfate; and 1,2-distearoyloxy-3-N,N,N-trimethylammoniumpropane chloride.

The dialkyl quaternary ammonium compound is typically present in the compositions of the invention at a level of from about 1% to about 30%, preferably from about 2% to about 25%, and more preferably from about 3% to about 20%, by weight of the composition.

Water-Soluble Active Material

The present compositions further comprise a water-soluble active material. The degree of hydrophilicity of an active material in the present compositions can be correlated with its octanol/water partitioning coefficient P. The octanol/water partitioning coefficient of an active material is the ratio between its equilibrium concentration in octanol and in water. An active material with a greater partitioning coefficient P is more hydrophobic. Conversely, an active material with a smaller partitioning coefficient P is more hydrophilic. Since the partitioning coefficients of active materials normally have high values, they are more conveniently given in the form of their logarithm to the base 10, logP.

The logP of many materials has been reported; for example, the Pomona 92 database, available from Daylight Chemical Information Systems, Inc. (Daylog CIS), Irvine, Calif., contains many, along with citations to the original literature. However, the logP values are most conveniently calculated by the "ClogP" program (calculation of hydrophobicities as logP (oil/water)) version 4.01, available from Daylight Chemical Information Systems Inc of Irvine Calif., USA. The ClogP values, which are the most reliable and widely used estimates for this physicochemical property, are used instead of the experimental logP values in the selection of water-soluble active materials which are useful in the present invention.

The water-soluble active materials in the present compositions have a ClogP of less than about 2.0, more preferably less than about 1.0.

Examples of water-soluble active materials include perfume raw materials ("PRMs"), cyclodextrins, biocides, fertilizers, drugs, and the like. Non-limiting examples of water-soluble perfume raw materials include beta gamma hexenol, coumarin, ethyl acetoacetate, and a mixture of 2 parts benzaldehyde, 2 parts beta gamma hexenol, 10 parts coumarin, 10 parts ethyl acetoacetate and 40 parts phenyl ethyl alcohol. Non-limiting examples of water-soluble cyclodextrins include hydroxypropyl beta-cyclodextrin. Non-limiting examples of water-soluble biocides include dodecyl trimethyl ammonium chloride, glutaraldehyde, and KATHON®.

The water-soluble active material is typically present in the compositions of the present invention at a level of from about 0.01% to about 10%, preferably from about 0.05% to about 5%, and more preferably from about 0.1% to about 2%, by weight of the composition.

In one embodiment of the present invention, the compositions are free of humectants, such as those described in WO 98/22085, WO 98/18444 and WO 97/01326, and/or emollients, such as those described in Sagarin, Cosmetics, Science and Technology, 2nd Edition, Vol. 1, pp. 32-43 (1972).

Water

The present compositions further comprise water, typically at a level of from about 60% to about 99%, preferably from about 70% to about 97%, and more preferably from about 75% to about 97%, by weight of the composition.

Adjunct Materials

The present compositions can optionally further comprise a number of various adjunct ingredients, depending on the type and use for the composition. In a preferred embodiment, the present compositions include fabric softening compositions for imparting softness and freshness (perfumes) to fabrics during a laundering process. Such compositions are typically added to the rinse cycle of a laundering process, although certain compositions can also be added during a wash cycle. Typical adjunct ingredients of fabric softening compositions are described in, e.g., U.S. Pat. Nos. 5,574,179;

5,562,849; 5,545,350; 5,545,340; 4,981,239; 4,767,547; 4,550,862; and U.S. Pat. No. 4,424,134.

The present compositions can also include hard surface cleaning compositions, such as for delivering water-soluble biocides or perfume materials to the surface being cleaned. Typical adjunct ingredients of hard surface cleaning compositions are described in, e.g., U.S. Pat. No. 5,382,376 and U.S. Pat. No. 4,111,854.

The present compositions can also include hair conditioning compositions, such as for delivering water-soluble perfume raw materials or cyclodextrins to the hair being treated. Typical adjunct ingredients of hair conditioning compositions are described in, e.g., U.S. Pat. Nos. 6,589,517; 6,468,515; and U.S. Pat. No. 5,876,705.

The present compositions can also include agrochemical compositions such as for targeted delivery of water-soluble biocides, fertilizer, or drugs to plant leaves and soil. Typical adjunct ingredients of agrochemical compositions are described in, e.g., U.S. Pat. No. 6,200,586; US 2003/0013799A1; and *Pesticide Formulation and Adjuvant Technology*, Edited by Chester L. Foy and David W. Pitchard, 1996, CRC Press Inc.

The present compositions can include paint compositions such as for delivery and adhesion of water-soluble biocides to the surfaces being painted, such as boat hulls. Typical adjunct ingredients of paint compositions are described in, e.g., U.S. Pat. No. 6,479,566; U.S. Pat. No. 6,242,526; WO 96/41842; and WO 97/00919.

Process of Manufacture

The vesicular compositions of the present invention are made by dispersing a molten dialkyl quaternary ammonium compound in water having a temperature above the transition temperature of the dialkyl quaternary ammonium compound under mechanical shear. The water temperature is kept above the transition temperature during the dispersion process to ensure the formation of a vesicular dispersion of the dialkyl quaternary ammonium compound.

The water-soluble active material to be delivered to the treated surface is preferably added to the hot water prior to the addition of the molten dialkyl quaternary ammonium compound. In an alternative process, the water-soluble active material is added together with or after the addition of the dialkyl quaternary ammonium compound to the hot dispersion, and the dispersion is kept hot for a sufficient time under mechanical shear to ensure the water-soluble active material is partioned into the intravesicular water domain.

The vesicular dispersion is subsequently cooled to ambient temperature, thus ensuring effective encapsulation of the water-soluble active material in the vesicles.

Test Method for Determining the Vesicle Permeability Index

A NMR diffusometry method provides information about the distances diffused by species in a component resolved manner. In a mixture of molecules, for example with water, surfactant and other solvents forming a vesicle dispersion, the method allows for determination of the diffusion rates of all components in the mixture. Due to the very high signal-to-noise of water, water is used to act as the probe for the permeability though the vesicle membranes. The component resolved signal decay in the NMR diffusometry experiment is impacted by the presence of barriers. In a concentrated mixture of vesicles the signal contains, roughly, two different types of water; water trapped inside and water outside the vesicles. Due to the chemical exchange, the fraction of water inside or outside depends strongly on the allowed diffusion time. Important to know is also that once a molecule from the inside leaves to the outside that water would appear to have belonged to the outside from the beginning. For the water initially outside, the situation is quite opposite. That water appears all the time to belong to the outside. In effect the signal from the water inside will decrease as the allowed diffusion time is made longer while the signal from the outside increases.

The ratio of the apparent volume fraction inside vesicles at a shorter diffusion time (e.g. 10 ms) over the apparent volume fraction at a longer diffusion time (e.g. 80 ms) gives therefore a measure of the vesicle permeability.

The vesicles in the present compositions have a particular permeability index, P, that is determined according to the following test method. Water diffusion inside and outside the vesicles is measured with Pulsed Field Gradient ("PFG") NMR and evaluated according to the methods described in "Colloids and Surfaces A, Diffusion of water in multilamellar vesicles of dialkyl and dialkyl ester ammonium surfactants", Cecilia Groth, Johanna Bender and Magnus Nydén (in press). Diffusion measurements are performed at 20° C. Diffusion times range from 10 ms up to 1 s using 5 different values logarithmically spaced between 10 and 80 ms. The pulsed field gradient strength is varied between 0.005 to 3.74 T/m with 45 linearly spaced gradient strengths spaced in-between (47 in total). The basic Hahn-echo sequence is used with $\delta=4$ ms and with varying diffusion times $\Delta=10, 20, 40$ and $80$ and for $\Delta=1000$ ms the stimulated echo-sequence is used.

From fitted values of the echo decay the apparent fraction of water in the vesicles at a specific diffusion time t can be calculated. The permeability Index, P, can then be calculated as $P_{vw}^{app}$ (10 ms)/$P_{vw}^{app}$ (80 ms).

As a non-limiting example, for a composition comprising HT-DEEDMAC at 20° C. the apparent fraction of water at $\Delta=10$ ms is $P_{vw}^{app}$ (10 ms)=0.28 and at $\Delta=80$ ms it is 0.49. The reason for this behavior is, as stated above, due to the finite gradient effect. The permeability index, as defined above then becomes $P_{vw}^{app}$ (10 ms)/$P_{vw}^{app}$ (80 ms)=0.28/0.49=0.57. Note that in this case the index is smaller than one due to the effect mentioned above in combination with the very slow water permeation.

EXAMPLES

Non-limiting examples of compositions of the present invention are provided in the following table as Examples 1-11. The compositions can be used as fabric softening compositions added during the rinse cycle of a laundering process to improve the softness and freshness of the fabrics being laundered.

|  | Ex. 1 | Ex. 2 | Ex. 3 | Ex. 4 | Ex. 5 |
|---|---|---|---|---|---|
| HT-DEEDMAC[1] | 5% | — | — | 5% | 5% |
| HT-TEAesterquat[2] | — | — | 5% | — | — |
| HT-PDesterquat[3] | — | 5% | — | — | — |
| Hydrochloric acid | 0.02% | 0.02% | 0.02% | 0.02% | 0.02% |
| Gluteraldehyde | 0.05% | 0.05% | 0.05% | 0.05% | 0.05% |
| Dye | 10 ppm | 10 ppm | 10 ppm | 10 ppm | 10 ppm |
| Perfume[4] | 0.3% | 0.3% | 0.3% | 0.17% | 0.3% |
| Water Soluble | 0.01% | 0.05% | 0.05% | 0.17% | — |
| Perfume Material | PRM1 | PRM2 | PRM3 | PRM4 | |
| Cyclodextrin[5] | — | — | — | — | 0.3% |
| Water | Balance | Balance | Balance | Balance | Balance |

|  | Ex. 6 | Ex. 7 | Ex. 8 | Ex. 9 | Ex. 10 |
|---|---|---|---|---|---|
| HT-DEEDMAC[1] | 15% | — | — | 15% | 15% |
| HT-TEAesterquat[2] | — | — | 15% | — | — |
| HT-PDesterquat[3] | — | 15% | — | — | — |
| Hydrochloric acid | 0.02% | 0.02% | 0.02% | 0.02% | 0.02% |
| CaCl[2] | 0.15% | 0.15% | 0.15% | 0.15% | 0.15% |

-continued

| | | | | | |
|---|---|---|---|---|---|
| Dye | 10 ppm | 10 ppm | 10 ppm | 10 ppm | 10 ppm |
| Perfume[4] | 0.9% | 0.9% | 0.9% | 0.5% | 0.9% |
| Water Soluble Perfume Material | 0.03% (PRM1) | 0.15% (PRM2) | 0.15% (PRM3) | 0.5% (PRM4) | — |
| Cyclodextrin[5] | — | — | — | — | 1.0% |
| Water | Balance | Balance | Balance | Balance | Balance |

[1]N,N-di(hardened tallowyl-oxy-ethyl)-N,N-dimethyl ammonium chloride.
[2]N,N-di(hardened tallowoyl-oxy-ethyl)-N-methyl, N-(2-hydroxyethyl) ammonium methylsulfate
[3]1,2-dihardenedtallowoyloxy-3-N,N,N-trimethylammoniumpropane chloride
[4]Water-insoluble perfume.
[5]Hydroxypropyl beta-cyclodextrin.
PRM1: beta gamma hexenol
PRM2: coumarin
PRM3: ethyl acetoacetate
PRM4: 2 parts benzaldehyde, 2 parts beta gamma hexenol, 10 parts coumarin, 10 parts ethyl acetoacetate and 40 parts phenyl ethyl alcohol.

In the following table, the composition of Example 11 is a preferred composition of the present invention wherein the composition is made by adding PRM4 to the hot product during formation of the vesicular dispersion, whereas the compositions of Examples 12 and 13 are made by adding PRM4 to the cold product after the vesicular dispersion is formed.

| | Ex. 11 | Ex. 12 | Ex. 13 |
|---|---|---|---|
| HT-DEEDMAC[1] | 10% | 10% | — |
| DEEDMAC[6] | — | — | 10% |
| Hydrochloric acid | 0.02% | 0.02% | 0.02% |
| CaCl$_2$ | — | — | — |
| Dye | — | — | — |
| Perfume[4] | 0.18% Ionone Gamma Methyl | 0.18% Ionone Gamma Methyl | 0.18% Ionone Gamma Methyl |
| Water Soluble Perfume Material | 0.32% (PRM4) | 0.32% (PRM4) | 0.32% (PRM4) |
| Cyclodextrin[5] | — | — | — |
| Water | Balance | Balance | Balance |

[1]N,N-di(hardened tallowyl-oxy-ethyl)-N,N-dimethyl ammonium chloride.
[4]Water-insoluble perfume.
[5]Hydroxypropyl beta-cyclodextrin.
[6]N,N-di(tallowyl-oxy-ethyl)-N,N-dimethyl ammonium chloride.
PRM4: 2 parts benzaldehyde, 2 parts beta gamma hexenol, 10 parts coumarin, 10 parts ethyl acetoacetate and 40 parts phenyl ethyl alcohol.

Example 14

In this example, 2 terry swatches of 40 grams each are rinsed for 5 minutes in 1 liter of tap water containing 2 ml of each of the compositions of Examples 11-13 above, and the terry swatches are subsequently spun dry in a commercial washing machine. The swatches are line dried overnight, and the odor impact of the swatches treated with the composition of Example 11 are compared to swatches treated with the compositions of Example 12 and 13 respectively.

The table below shows a higher odor impact for the terry swatches treated with the preferred compositions of the invention.

| | Ex. 11 | Ex. 12 | Ex. 13 |
|---|---|---|---|
| Damp Fabric Odor | +4 | Ref. | — |
| Odor on Dry Fabrics | +3 | — | Ref. |

Scale used:
+3 = slightly stronger;
+5 = stronger.

All documents cited in the Detailed Description of the Invention are, in relevant part, incorporated herein by reference; the citation of any document is not to be construed as an admission that it is prior art with respect to the present invention.

It should be understood that every maximum numerical limitation given throughout this specification includes every lower numerical limitation, as if such lower numerical limitations were expressly written herein. Every minimum numerical limitation given throughout this specification includes every higher numerical limitation, as if such higher numerical limitations were expressly written herein. Every numerical range given throughout this specification includes every narrower numerical range that falls within such broader numerical range, as if such narrower numerical ranges were all expressly written herein.

While particular embodiments of the present invention have been illustrated and described, it would be apparent to those skilled in the art that various other changes and modifications can be made without departing from the spirit and scope of the invention. It is therefore intended to cover in the appended claims all such changes and modifications that are within the scope of this invention.

What is claimed is:

1. A process comprising the steps of:
   a) dispersing under mechanical shear a molten dialkyl quaternary ammonium compound selected from the group consisting of N,N-di(stearoyl-oxy-ethyl)-N,N-dimethyl ammonium chloride; N-stearyl-N-(stearoyl-oxy-ethyl)-N,N-dimethyl ammonium chloride; N,N-di(stearoyl-oxy-ethyl)-N-methyl,-N-(2-hydroxyethyl) ammonium methylsulfate; 1,2-distearoyloxy-3-N,N,N-trimethylammoniumpropane chloride; N N-di (hardenedtallowovl-oxv-ethyl)-N,N-dimethyl ammonium chloride; N-hardenedtallowvl -N-(hardenedtallowovl-oxv-ethyl)-N,N-dimethyl ammonium chloride; N,N-di (hardenedtallowovl-oxv-ethyl)-N-methyl-N-(2-hydroxyethyl) ammonium methyl sulfate; 1,2,-hardenedtallowoyloxy-3-N,N,N-trimethylammoniumpropane chloride; and mixtures thereof in hot water having a temperature above a transition temperature of said dialkyl quaternary ammonium compound;
   b) adding a perfume raw material to said dialkyl quaternary ammonium compound to form a mixture;
   c) dispersing said mixture into water having a temperature above a transition temperature of said dialkyl quaternary ammonium compound; and
   d) cooling said mixture to form a composition comprising vesicles having a vesicle permeability index of less than about 1.3 and perfume raw material; wherein the mixture formed by step (b) is formed either by;
   (i.) adding the perfume raw material to said hot water prior to the addition of the molten quaternary ammonium compound; or by
   (ii.) adding the perfume raw material to said hot water together with or after the addition of the molten quaternary ammonium compound.

2. The process of claim 1 wherein said vesicle permeability index of said vesicles is less than about 1.1.

3. The process of claim 2 wherein said vesicle permeability index of said vesicles is less than about 1.0.

4. The process of claim 3, wherein said purfume raw material has a ClogP of less than about 1.0.

5. The process of claim 1 wherein said dialkyl quaternary ammonium compound is present at a level of from about 2% to about 25%, by weight of the composition.

6. The process of claim 5 wherein said dialkyl quaternary ammonium compound is present at a level of from about 3% to about 20%, by weight of the composition.

7. The process of claim 1 wherein said composition is a fabric softening composition.

8. The process of claim 1 wherein said composition is a hard surface cleaning composition.

9. The process of claim 1 wherein said composition is a hair conditioning composition.

10. The process of claim 1 wherein said composition is an agrochemical composition.

11. The process of claim 1 wherein said composition is a paint composition.

* * * * *

UNITED STATES PATENT AND TRADEMARK OFFICE
CERTIFICATE OF CORRECTION

PATENT NO. : 8,506,940 B2
APPLICATION NO. : 12/793912
DATED : August 13, 2013
INVENTOR(S) : Demeyere et al.

It is certified that error appears in the above-identified patent and that said Letters Patent is hereby corrected as shown below:

In the Claims

Claim 1
Col. 8, Lines 33-37, delete "N N-di (hardenedtallowovl-oxv-ethyl)-N,N-dimethyl ammonium chloride; N-hardenedtallowvl-N-(hardenedtallowovl-oxv-ethyl)-N,N-dimethyl ammonium chloride; N,N-di(hardenedtallowovl-oxv-ethyl)" and insert -- N,N-di(hardenedtallowoyl-oxy-ethyl)-N,N-dimethyl ammonium chloride; N-hardenedtallowyl-N-(hardenedtallowoyl-oxy-ethyl)-N,N-dimethyl ammonium chloride; N,N-di(hardenedtallowoyl-oxy-ethyl) --.

Claim 4
Col. 8, Line 63, delete "purfume" and insert -- perfume --.

Signed and Sealed this
Fifteenth Day of October, 2013

Teresa Stanek Rea
*Deputy Director of the United States Patent and Trademark Office*